United States Patent
Fabrizio (10) Patent No.: US 8,899,832 B2
(45) Date of Patent: Dec. 2, 2014

(54) MOBILE PATIENT POSITIONING SHIELD FOR MULTIPLE EXPOSURE IMAGING EXAMS

(71) Applicant: Robert A. Fabrizio, Stamford, CT (US)

(72) Inventor: Robert A. Fabrizio, Stamford, CT (US)

(73) Assignee: Fujifilm Medical Systems U.S.A., Inc., Stamford, CT (US)

( * ) Notice: Subject to any disclaimer, the term of this patent is extended or adjusted under 35 U.S.C. 154(b) by 278 days.

(21) Appl. No.: 13/633,796

(22) Filed: Oct. 2, 2012

(65) Prior Publication Data

US 2013/0101088 A1  Apr. 25, 2013

Related U.S. Application Data

(60) Provisional application No. 61/549,551, filed on Oct. 20, 2011.

(51) Int. Cl.
| | |
|---|---|
| H05G 1/02 | (2006.01) |
| A61B 6/08 | (2006.01) |
| A61B 6/04 | (2006.01) |
| A61B 6/06 | (2006.01) |
| A61B 6/00 | (2006.01) |
| A61B 6/12 | (2006.01) |

(52) U.S. Cl.
CPC ............... *A61B 6/08* (2013.01); *A61B 6/0492* (2013.01); *A61B 6/06* (2013.01); *A61B 6/4452* (2013.01); *A61B 6/5241* (2013.01); *A61B 6/12* (2013.01)

USPC ............ 378/196; 378/195; 378/203; 378/208

(58) Field of Classification Search
CPC .... A61B 6/5241; A61B 6/4452; G03B 42/02; H04N 5/32
USPC .................. 378/195, 196, 203, 208
See application file for complete search history.

(56) References Cited

U.S. PATENT DOCUMENTS

| | | | |
|---|---|---|---|
| 7,555,100 B2 | 6/2009 | Wang et al. | |
| 7,742,570 B2 * | 6/2010 | Yamaguchi | ................ 378/98.12 |
| 2009/0238341 A1 | 9/2009 | Kawamura | |
| 2011/0038454 A1 | 2/2011 | Minnigh et al. | |
| 2011/0064193 A1 | 3/2011 | Minnigh et al. | |
| 2012/0059239 A1 | 3/2012 | Yamaguchi | |

* cited by examiner

*Primary Examiner* — Michael Maskell
(74) *Attorney, Agent, or Firm* — Blakely, Sokoloff, Taylor & Zafman LLP (57) ABSTRACT

A mobile patient positioning stand having vertical rails allowing a shield to be manually moved up and down to different heights based on the height of anatomy of the patient desired to be imaged. The shield may be positioned at a shield height for a certain height of anatomy of a patient so that markers on the shield identify multiple image areas within the total image area. After the shield is positioned, an image detector and a source of radiation may be vertically positioned to provide images at the multiple image areas. Vertical positioning of the detector may be determined by the markers or by equal height detector alignment markers on the shield. The multiple image areas may be connected by aligning stitching markers in the images, that may be on the shield. This aligning may be done by an automated computer software process that recognizes the stitching markers.

23 Claims, 4 Drawing Sheets

MOBILE PATIENT POSITIONING SHIELD FOR MULTIPLE EXPOSURE IMAGING EXAMS

This is a non-provisional application claiming the benefit of U.S. Provisional Application No. 61/549,551, filed Oct. 20, 2011.

FIELD

Embodiments of the present invention relate to patient positioning shields for radiographic long length imaging, such as devices used to correctly mark borders of multiple images taken with a flat panel detector, so that the images can be properly aligned to form a longer length image area. Other embodiments are also described.

BACKGROUND

Medical radiographic imaging systems may apply radiation, such as x-rays, to a patient and detect radiation passing through the patient to obtain a radiographic image for diagnosis. In recent years, flat panel-type detectors have been used to detect a radiation image of a patient irradiated by a source (e.g., an x-ray tube). For some radiographic exams, multiple exposures may be needed to form an extended field of a long length image, due to the image detector having a smaller size than the long length image desired. Some types of desired exams associated with this type of extended field of view capture are exams such as: spine and scoliosis, long leg, and whole body imaging.

For example, traditional indirect forms of x-ray capture for such multiple captures may be achieved by overlapping multiples of analog x-ray film or re-useable computed radiography (CR) imaging plates, orienting them in one long length arrangement. Then a single exposure may be taken to expose all the capture areas at the same time. Resulting individual images can be processed separately (one at time) to transfer them to a processing workstation to be connected or stitched together.

In recent years, x-ray capture devices (e.g., detectors) have included portable electronic flat panel detectors which are directly connected (wired or wirelessly) to the workstation for immediate image transfer to the workstation (e.g., this provides "direct x-ray capture"). However, detectors may be significantly more expensive than film and it is less common to have multiple detectors. In addition, from the mechanical characteristics of their design it is not currently feasible to overlap them for a single long length exposure capture, since they consist of elaborate electronic components and surrounding structural hardware. Also an extended long sized (e.g., direct long length) detector may not be feasible for user versatility or cost.

This means that a long length capture requires separate multiple captures or images at sequential detector positions. Capturing multiple images separately introduces challenges in moving the detector behind the patient between each exposure. For example, upright x-ray exams are commonly performed using an upright or chest detector stand with some type of detector or image capture device inside. These upright devices feature the ability to position the detector at various heights depending on anatomy of interest and patient size. Some exams require multiple images at different heights to view a longer area of interest. It is preferable for these multiple images to be connected or "stitched" together as one extended length image.

SUMMARY

Embodiments of the invention provide improved systems, apparatus, and methods of use of a mobile patient positioning stand for multiple exposure imaging exams. In some cases, such a stand may be described as "a mobile stitching shield" since it includes a mobile frame having a moveable patient positioning shield to be manually positioned at different heights based on the height of anatomy of the patient desired to be imaged, and based on a desired total image area (e.g., an image field) of a long length capture or image. The shield may be vertically positioned at a height so that markers on the shield identify multiple image areas of desired images within the total image area desired for a certain height range patient anatomy desired to be imaged. Multiple image areas may be needed due to use of an image detector of having a vertical size less than the desired total vertical image area size. After the shield is positioned as desired, a source of radiation and the image detector may be vertically positioned to provide images at the multiple image areas within the total image area. The vertical positioning may be determined by the markers on the shield. The multiple image areas may be identified in the images by the markers on the shield. After the images are generated, each image area may be connected to other image areas of the patient to form a total image area, such as a radiographic long length image.

FIGURES

The embodiments of the invention are illustrated by way of example and not by way of limitation in the figures of the accompanying drawings in which like references indicate similar elements.

DETAILED DESCRIPTION

Several embodiments of the invention with reference to the appended drawings are now explained. Whenever the shapes, relative positions and other aspects of the parts described in the embodiments are not clearly defined, the scope of the invention is not limited only to the parts shown, which are meant merely for the purpose of illustration. Also, while numerous details are set forth, it is understood that some embodiments of the invention may be practiced without these details. In some instances, well known components or methods have not been described in detail in order to avoid unnecessarily obscuring the present invention. Similarly, in some instances, well-known circuits, structures, and techniques have not been shown in detail so as not to obscure the understanding of this description.

When using a radiographic detector smaller than a desired total vertical image height, a long length image may be obtained by connecting multiple images taken of image areas over a total image area. Markers or screen printed hair lines disposed on a shield between the patient and detector may provide marks for alignment of the images by being shown in the overlapping parts of the images together with the subject. The images may be connected or "stitched" together based on these markers being positioned at borders of image areas or frames. In some cases, the images can be aligned without markers simply based on a specified amount of image to image overlap (e.g., the height of image that exists in each image, beyond the markers). Thus, a patient "positioning stand" having a shield with the markers and or simple alignment lines may be used for multiple image exposures during imaging of a total image area, long length image or long length capture field.

Consequently, for these exams to work optimally, the patient should remain as still as possible for each capture exposure, so that anatomy in the image areas align well when stitched together. In these exams, it may be quite difficult for the technologist or user to accurately identify correct positions of the images (e.g., image areas), and amount of overlap of the images, when moving the detector to the next exposure position or location. If either of these are not accurate, the markers could miss the detector (e.g., not exist within the size of the detector) in one exposure or the other, or the amount of image overlap of adjacent images may not line up well enough for the software to automatically perform the stitching processing optimally.

Some positioning stands have been designed primarily just for patient position shielding and are utilized in conjunction with automated detector positioning systems where the detector movement accuracy is determined by synchronized automated motorized positioning of the detector elevation and tube alignment. However, these stands do not provide usability for manually operated upright devices which are more common and less expensive. They also do not feature height adjustment of the glass shield, which assists in simplifying the alignment markers to the patient height. Some stands similar to this do not feature markers to align a manually operated detector system.

Embodiments of the invention are designed to perform multiple image captures for extended field of view exams utilizing a portable digital x-ray detector or a fixed detector device or with traditional CR or analog film screen cassettes. Embodiments include a "portable" or "mobile" patient positioning stand designed for use with customer's existing upright chest stand (AKA Chest Bucky device), digital capture device such as a flat panel detector or CR cassette combined with the associated computerized image processing workstation. The stand includes a shield that helps steady the patient while multiple exposure exams are taken, such as to capture long view images. Typical digital x-ray workstations feature the ability to display, reprocess and send images to diagnostic workstations. In some embodiments, the alignment between vertically adjacent images is recognized by the capture workstation software, by utilization of special shape lead markers. An "X" or "+" plus sign maker may be positioned on the right and left side of the outer edge of the area of the shield or screen (e.g., at a horizontal outer border of the shield) where the multiple images will be captured at an overlap to each other (e.g., at vertical borders between and included in adjacent images). Once the separate images are captured, the software looks for the markers and lines them up with the sequential images captured to accurately reproduce the overlap and align them together. Moreover, the stand or shield may be described as "universal" since it can be used with various chest stands, such as by including markings on the shield at different heights (or that are moveable to different heights) such that the markers will identify borders of image areas for various sized detectors and/or for detectors at different orientations.

Some embodiments of the invention provide a mobile frame having a shield that is movable (e.g., manually) on the stand and that has marker locations to simplify multiple detector positions for upright x-ray exams. The mobile shield may be positioned in front of the detector bucky (detector holder) of a typical x-ray chest stand, to simplify and speed guidance of accurate position of the detector for each of the desired separate adjoining images. They further conveniently adjust detector positioning markers to match desired field of view to patient height for proper detector anatomy height positioning, such as due to easy manual positioning of the shield height. The stand's shield also shields the patient from detector movements hitting them. They also help the patient remain steady and in proper position during the exam, by allowing patient to stand up against the shield, along with optional armrests which can further steady the patient. They simplify detector alignment position accuracy for the multiple exams by use of lines or markers on the shield to quickly guide where the detector bucky should be aligned for proper overlap amount for each exposure and may also include lines to help simplify alignment of the x-ray tube to the center of each capture area (e.g., image area) and may also simplify where the user can place special "moveable" stitching markers (optional) to accurately align with overlap areas of adjoining image/detector positions.

Figure 1:
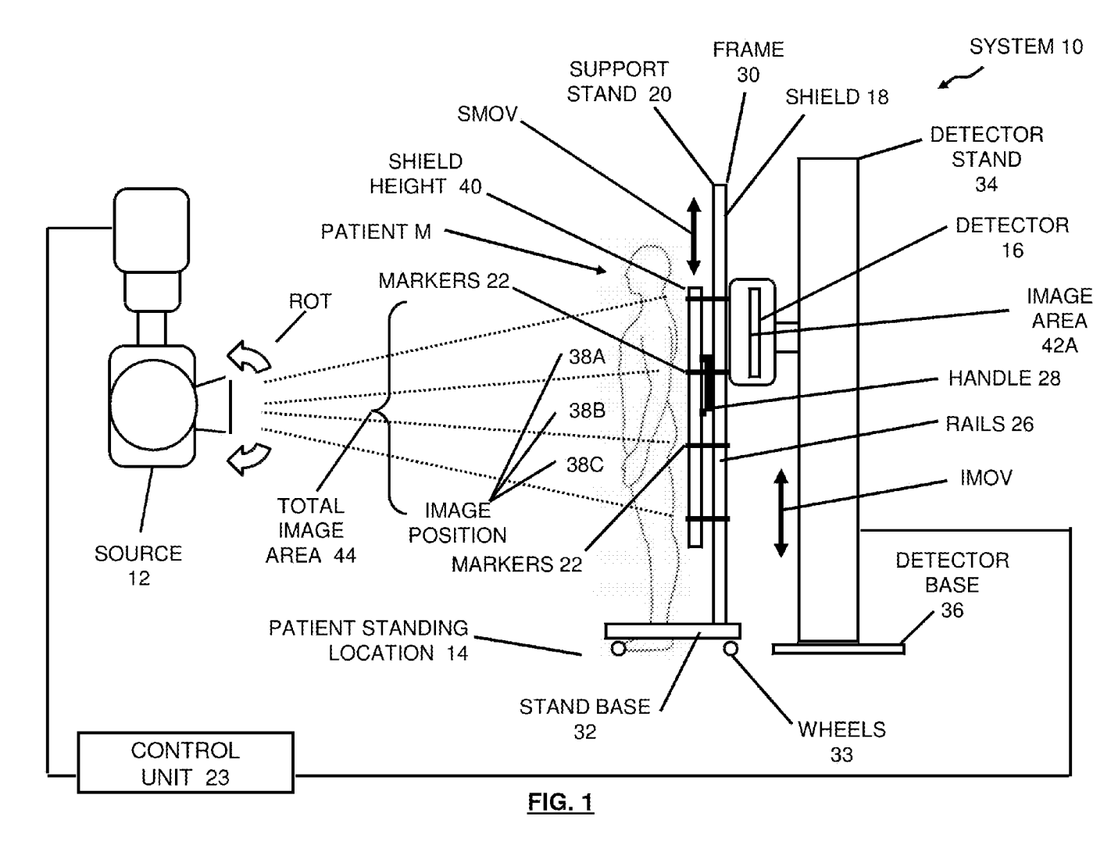
FIG. 1 shows example embodiments of a patient positioning system for multiple image areas of a total radiographic image area or field.

FIG. 1 shows example embodiments of a patient positioning system for multiple image areas of a total radiographic image area or field, such as of a desired long length image. In FIG. 1, system 10 is shown including radiation (e.g., x-ray) source 12 to irradiate patient M, standing at patient standing location 14 of patient positioning stand 20, to form an image using image detector 16. Detector 16 may be part of any traditional chest stand imaging device. Mobile stand 20 may be positioned, close to without touching, just in front of the detector holder 36 of the chest stand. System 10 includes stand 20 with manually movable shield 18 having radiographic imagable markers 22, such as markings on front or outer or rear surface (or adhered directly to the front of the detector), such as for identifying or marking borders of radiographic image areas (e.g., areas 42A-C) of total image area or field 44. In some cases, each image area 42A, B and C may correspond to an image position of source 12 and detector 16, such as during x-ray exposure imaging or exams. Total image field 44 is longer than a length of any single one of image areas 42A-C, and each image area of areas 42A-C corresponds to one of image positions 38A-C of field 44. In some cases, positions 38A-C may be selected by rotating the angle of the radiation output of source 12 along vertical rotational direction ROT to a proper centering to irradiate each image area (e.g., source 12 rotates around a horizontal axis going into the page of FIG. 1) and moving detector to a corresponding height for imaging image area 42A-C. Source 12 position could also be achieved by vertical up or down movement of the x-ray source 12, however rotation may be preferred for optimal imaging. Markings or hash marks on the stand shield or edges may be included (such as markers 22, lines 24 or pointers 25) to help simplify accurate centering of x-ray source with each image field by using the x-ray source's centering laser. Each image area may correspond to or represent an image of patient M to be connected to at least one other image of the patient (corresponding to an adjacent image area) to form total image area 44.

Stand 20 is shown including frame 30 having manually movable shield 18 to provide (e.g., vertically moveable) markers at positions on the shield. The markers may be x-ray transparent (do not show in captured images) markings for detector positions, such as at borders of image areas 42A-C, between source 12 and detector 16 and center of overlap areas for placement of processing software identifiable makers (x-ray image able markers) and markings for tube laser alignment to the center of image areas. Marker positions in images of image areas 42A-C can be used for connecting (e.g., overlapping or stitching) the images, such as based on the marker positions within the overlap are of each adjoining image.

Shield 18 may include a flat or planar surface of a radio transparent material such as glass, or another material as know in art. Markers 22 may be attached to or formed on surfaces of the shield, such as the front, side and/or back of the shield. Markers 22 may be or include a material having a large enough radiographic attenuation to be radiographic imagable or recognizable by software in a radiographic image. Markers 22 may be or include "stitching markers" as known in the art. Markers 22 may be fixed or removable as described further herein. In some embodiments, shield 18 may have a base platform or step for supporting a patient, as know in the art. Shield may include handle 28 to allow the operator to easily slide the shield indirection SMOV along shield height 40 (e.g., vertically moveable) to provide one or more types of markers at positions on the shield. These markers may include x-ray transparent markings (do not show in captured images, such as lines 24) for identifying detector positions, such as at borders of image areas 42A-C, between source 12 and detector 16; and for identifying center of image overlap areas to identify placement of processing software identifiable makers (e.g., x-ray image able markers, such as markers 22) or markings may be placed on outer edges of shield or shield frame or and markings for tube laser alignment to the center of image areas. Marker 22 positions in images of image areas 42A-C can be used for connecting (e.g., overlapping or stitching) the images, such as based on the marker positions within the overlap are of each adjoining image. In some cases, height 40 represents the height from the floor (or a platform the patient stands on) to the top of the shield. Handle 28 may represent one handle on a side surface of the shield, two handles (one on each side), or may represent a grip area for the user to easily grip the shield (e.g., one or both sides with a hand) without interfering with the patient, detector or stand positions. In some case, the shield includes a location and ability to be manually gripped by a user to vertically move the shield along the rails, to locate the shield at a desired shield height that positions the markers at vertical borders of the image areas.

Shield 18 is movingly coupled to rails 26 of stand 30 or may be directly slidably mounted between the rails, or similar. For example, frame 30 is shown with shield 18 movably mounted on or mounted between two parallel rails 26 which are mounted on a stand base 32 having wheels 33. The base may have arms with wheels 33 for rolling on a floor. Thus, stand 20 may be moved across a floor of rooms and down hallways, such as to be moved to and used in different rooms of a medical facility. In some embodiments, there may not be any wheels, such as where the base has legs that stand on a floor. In this case, stand 20 may be mobile by being picked up and carried from one location to another. Rails 26 are shown attached to top strap 31 (see FIGS. 2A-B). It is considered that other forms of framework may be used to support shield and its movements (e.g., other than top strap). Mounting of rails 26 to base 32 and strap 31 maintains a parallel disposition of rails 26 so that shield 18 can be moved by the user along vertical height SMOV (e.g., slidably moved along a vertical axis) to shield height 40 of possible shield heights 41 (see FIGS. 2A-B). In some cases, heights 41 represent a range of heights of the top of the shields. Heights 41 may be selected to provide enough range for a selected desired image area and height of patients. Shield 18 may be described as an imaging or patient support "member" or "screen".

Figures 2A, 2B:
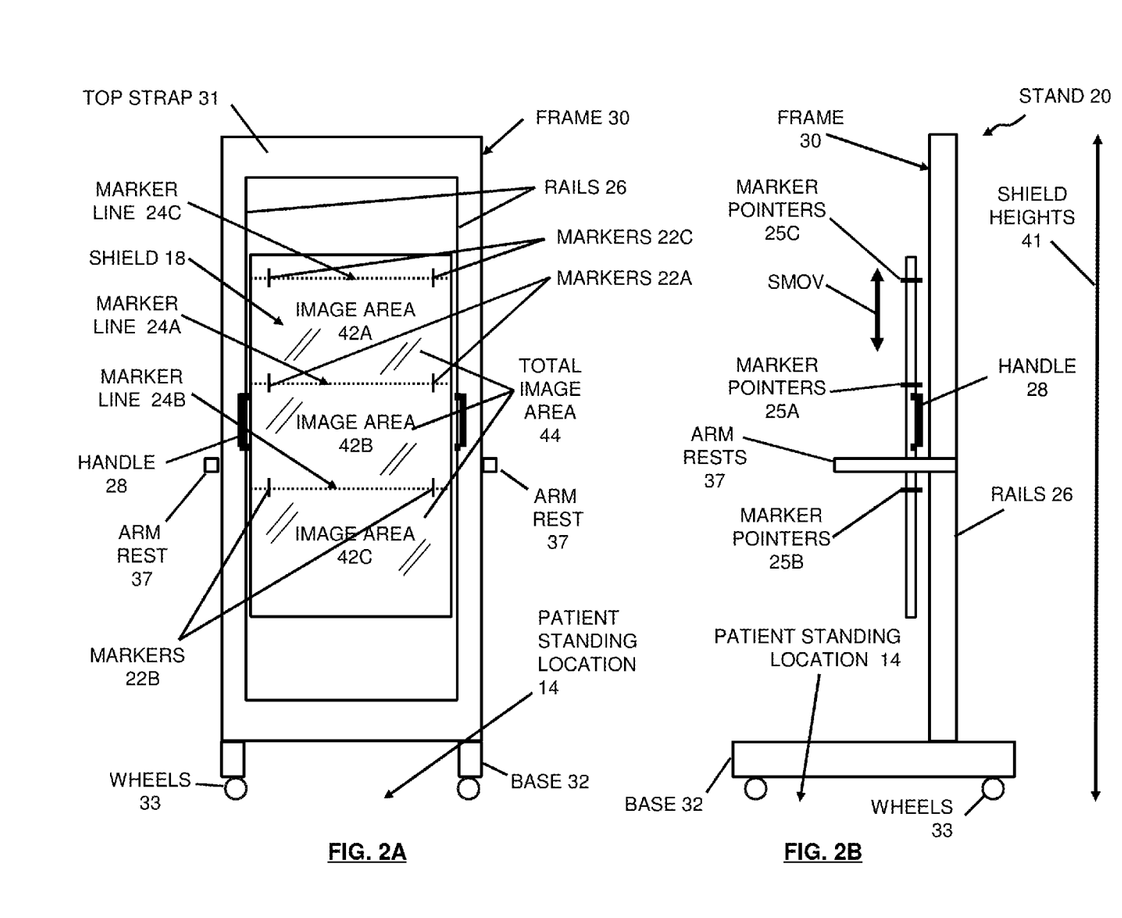
FIG. 2A shows a front view of example embodiments of a patient positioning stand for multiple image areas of a total radiographic image area or field.
FIG. 2B shows a side view of example embodiments of a patient positioning stand for multiple image areas of a total radiographic image area or field.

Total image area 44 may correspond to or cover a desired total image area of a patient to be imaged during an imaging exam. Area 44 may be selected by vertically moving shield 18 in directions SMOV on or along vertical rails 26 to shield height 40 using handle 28 so that at height 40, the shield provides at least two or three vertically adjacent image areas (e.g., of areas 42A-C) that are centered on the desired total image area. Vertically positioning shield 18 so that shield height 40 provides these image areas may be dependent upon or based upon the total height of patient M. In some cases, the shield 18 may be moved to (or positioned at) a shield height 40 that is selected based on a height of anatomy of a patient that is desired to be imaged (e.g., in the desired total image area). It can be appreciated that for the same anatomy desired to be imaged, the height of that anatomy may be different for different patients. This may be due to different patients having different height, and/or having the same anatomy at different heights, and to accommodate for long length images of upper or lower body areas (e.g., even for same height patients). In certain cases, the shield 18 may be positioned at a shield height 40 such that a vertical range of anatomy of a patient that is desired to be imaged is within a desired total vertical image area of the shield. In some cases, selecting shield height 40 may include vertically aligning markers 22, of one or more adjoining image areas, to be above and below a height of anatomy of a patient that is selected to be imaged in a desired long length image. In some cases, frame 30 and shield 18 will be have a total vertical size (or height) so that possible shield heights 41 and the vertical size of shield 18 are sufficient to image a desired extended field of view or vertical height of a person's anatomy for a long length imaging exam, such as known in the art. In some cases, heights 41 extend from a height of the shield that images from as low as the floor up 2-3 images or more or starting from top height of to up to a height of for example 6 foot 6 inches in height (depending on height of stand which can be design in different heights) and imaging 2-3 images or more in length down. Area 44 may be a portion or a subset of the maximum image height field provided by heights 41. Sequence or travel direction up or down from one image to the next may be irrelevant to the stand design (image processing software may have a preference for easier combining of the images). The patient's height or the height of anatomy of a patient that is desired to be imaged may be determined by a prior height measurement or by the height observed by the user while the patient is actually standing at location 14. In some cases, the height of anatomy of a patient may be determined by the user, as known in the art. In some cases, the height of anatomy of a patient may be determined based on internal and/or external anatomy of the patient. After the imaging exam, the shield may be moved to a different shield height for a subsequent exam of a different height patient.

Wheels 33 allow stand 20 to roll along or be moved across a floor. Wheels 33 may be castors having rotational locks, as know in the art. Thus, stand 20 may be a "portable", "mobile" or "moveable" stand that can be moved between different exam rooms and/or can be used with different source and detector systems. Wheels 33 may be optional, and base 32 may be fixed to or slide-ably mounted (or otherwise movable) on the floor. Additionally a patient step platform may optionally be used between the legs of the stand base (32) to raise the viewability of the patient's feet to a desired height above the floor.

According to embodiments, stand 20 is horizontally positioned (e.g., rolled or positioned horizontally) between detector 16 (e.g., detector stand 34) and source 12 so that shield 18 (or image areas of the shield) is horizontally centered with the horizontal center or axis of an image taken when irradiating the detector with the source. Then Patient M may be horizontally located (e.g., moved or positioned horizontally) at patient standing location 14, between shield 18 and source 12 so that the areas of the patient to be imaged are horizontally centered with the horizontal center or axis of the image areas of the shield. This may include arranging the patient in a standing position. Positioning the patient may also consider horizontally positioning the patient between detector 16 and source 12 so that areas of the patient to be imaged are horizontally centered with the horizontal center or axis of an image taken when irradiating the detector with the source. In some cases, the patient is horizontally aligned between the source and the shield (and detector) so that a desired total image area is centered within horizontal center of the actual total image area 44. The desired total image area may be a planned long length image area, such as known in the art. It may also be based on a user's determination (e.g., an x-ray technologist or radiologist) of examining the patient while the patient is at location 14.

Detector 16 may be an image radiation detector or image sensor (e.g., within a typical chest stand imaging device) able to produce images of the image areas (fields or frames). The images may be connected by stitching together or combining the adjoining images, such as by overlaying vertical borders of the images with or without the use of software recognizable markers so that the markers shared by overlapping borders of vertically adjacent areas are overlaid in the images to correctly match alignment from one image to the next. For instance each of a plurality of the radiographic images (of image areas) may partially overlap another image at the overlapping parts within total image field 44. Stand 20 provides radiographic image areas for the total image field 44 of a patient, the total image field being longer than a length of each image (a maximum field of view of an imager, radiation detector or sensor to produce images of an image area or field). In some cases, each image area may be equal to the maximum field of view, image area, or surface area of the detector.

Source 12 may rotate to positions in a range between the minimum and maximum height of detector 16 locations. Source 12 position could also be achieved by vertical up or down movement of the x-ray source 12 to aligned the output with vertical elevation (instead of tube rotation) height centering for each separate image. However rotation is typically preferred for optimal imaging. In some cases, the source of radiation is positioned at a vertical height that is a same height as a center height of the total image area to be imaged, and then tube angle is rotated to center the radiation output to each exposure area. Source 12 may be an x-ray source, such as a radiation source for imaging as known in the art. In some cases, source 12 may be a source for traditional CR or analog screen film screen cassette imaging x-ray system, as known in the art.

FIG. 1 also shows detector 16. Detector 16 may be movably mounted on a separate detector stand 34 having base 36, as known in the art. The detector and the mounting of the detector on stand 34 may include structures known in the art for flat panel detectors. Such mounting may include structures for mounting of direct x-ray capture flat panel detectors or CR computed radiography or analog film cassette, such as detectors that can be removed from stand 34 and used in another stand, or the stand can feature a fixed built-in (not removable) detector. Base 36 may be permanently or slidably mounted on the floor. Detector 16 may be constructed in such a manner that it can move along a supporting column of stand 34 provided in parallel to the body axis of the patient. In some cases, the detector stand is bolted to floor, is not integrated with, and not part of the positioning stand 20 structure. Detector may be vertically slidable in directions IMOV along a vertical axis. In some cases, the vertical axis that the shield is moveable on (in directions SMOV) may be parallel to the vertical axis for the detector.

In some embodiments, during exam, first the shield height is set to preferred range of anatomy coverage area (once set to this "patient's height" for the desired region of interest, the shield height stays at this height for the entire sequence of images) then the chest stand's detector holder/bucky is manually aligned to corresponding markings on the stand (e.g., markings 22, 24 and/or 26) for each image to be captured. Shield height may be adjusted by manual sliding movements within the outer shield rails. Rail friction and/or counteraction by way of flat coil spring or other known mechanisms may be included to simplify movements and counterbalance weight of typical detector and optional grid. Some embodiments may include motorized or "free fall" movement for the shield and with or without locking positions. In some cases, stand 20 features motorized shield elevation movements which can be controlled by button controls mounted to the stand, or by wireless or wired remote hand or foot switches. The movement may be moved by motors and/or other components of stand that are connected to such controls.

In some embodiments, the user manually adjusts the height of detector 16 by moving it along vertical direction IMOV, over a range of detector heights for patient M during the x-ray exam. Detector 16, or the moveable mount of the detector may include a handle for such manual movement. The height of the detector may be moved to locate the detector at a detector height position determined by or based on the positions of markers 22 on the shield (e.g., once the shield is positioned at height 40 as noted herein). In some cases the detector is positioned to image an image area as described herein. Once the shield is at height 40, the detector may be moved to different detector height position to image different, subsequent image areas (e.g., of areas 42A-C) while the shield stays at the same height 40, for a patient. Markers 22 or 24 may be used to identify a vertical height for alignment of the detector (e.g., to one or more borders of an image area; or to a center of an image area), such as by aligning a vertical edge of the detector with a height of markers 22 or by aligning center lines of shield to center lines of the detector or by utilizing the source laser alignment to assist in visibility of alignment of detector and shield center lines for an image area. This may be done to align the detector for proper overlap amount for each exposure, and/or for alignment of images. This may include aligning the detector to provide a proper overlap amount of each image so that the adjacent images can be aligned and combined. In some cases, alignment of the detector may be based on or may include being based on the height of anatomy of the patient that is desired to be imaged. In some embodiments the shield may be moved to a height so that markers 24 and/or 25 can be used to aligning an image detector to correct positions for imaging vertically adjacent and partially overlapping images of vertically adjacent image areas of a desired total image area of the patient.

For instance, the detector may be vertically aligned or positioned so that the top, bottom or middle of the detector is vertically aligned with one of markers 22 (e.g., such as by being vertically aligned with one of lines 24 and/or pointers 25 based on a user's observation). In some cases the detector may be vertically positioned to, or be vertically aligned with (e.g., relative to) more than one of lines 24 and/or pointers 25. This may include selecting two of lines 24 and/or pointers 25 from the top, bottom or middle of the image area are vertically aligned with two positions (e.g., at top, bottom or middle) of the detector. There may be markers or markings on the front and/or sides (e.g., at top, bottom or middle) of the detector to align with the markers or markings on the shield. In some cases, the pointer markers are disposed on the shield face and or outer side edges of the shield to assist a user in vertically locating the detector to a correct vertical position based on the pointer markers for aligning an image detector to correct positions for each image capture area.

In some embodiments, the detector may be "automatically" vertically moved or positioned along direction IMOV as noted herein. The movement may be controlled by control unit 23 or buttons connected to the stand, and moved by motors and/or other components of stand 34. This may be done, as known in the art. In some cases, this may be based on the height of markers 22.

Detector 16 may be a radiographic image "imager" or "sensor" as known in the art. In some cases detector may be a flat panel radiographic detector, or a radiographic image sensor to produce image of an image area or field equal to or just smaller than the total surface area of the detector. In some cases, detector 16 may be a detector for traditional CR, a re-useable computed radiography (CR) imaging plate, or an analog x-ray film screen cassette, as known in the art. In some cases the detector may be a customer's existing upright chest stand (AKA Chest Bucky device), digital capture device such as a flat panel detector (fixed or removable) or CR cassette combined with the associated computerized image processing workstation, as known in the art.

In some embodiment shield 18 may be positioned in front of a typical upright x-ray capture device 16 such as a conventional upright "bucky" image detector stand 34 with base 36. An embodiment of the invention features sliding shield 18 (e.g., a glass shield) which the x-ray technologist (e.g., user) adjusts by manually moving shield 18 (such as using handle 28) in vertical directions SMOV over shield height 40 for the height of the patient M that stands in front of the stand and shield for the x-ray exam. The glass may have marker lines and stitching markers (e.g., see FIGS. 2A-B) to guide where to vertically position detector 16 (e.g., a "bucky" detector) behind the shield for the desired sequence of exposures (e.g., images of areas 42A-C).

Thus, the Mobile Shield design may not feature a detector holder. The detector holder may be the detector bucky of a separate typical chest stand imaging device. Movement of the chest bucky from one image to another may be determined by the chest stand model. Many chest stands feature manual movements. Some chest stands feature motorized elevation movements which can be by button controls mounted to the chest stand, or by wireless or wired remote hand or foot switches.

In some cases, control unit 23 is not connected to the stand. The control unit as in known art is connected to the source generator, it sets exposure techniques and triggers exposure. In some cases, the detector is connected to generator exposure activation to trigger it's capture. In some cases, the detector user workstation is connected to the control unit 23 to simultaneously control other automation such as x-ray source and detector repositioning movements from one capture to the next, such as as known in the art. Workstation may also through communication to the Control unit 23, control presetting preferred exposure technique settings, start, exposure duration, beam filtering, and other processing of radiation detection by detector 16. In the example of DR digital capture detectors, image signals output by the detector are converted to digital data and transmitted to the workstation via wired or wireless connection where images are previewed and subjected to image processing, including combining of images of image areas and sent to other workstations for diagnosis and archiving.

FIGS. 2A-B show front and side views of example embodiments of a patient positioning stand for multiple image areas of a total radiographic image area or field. FIGS. 2A-B show frame 30, top strap 31, armrests 37, markers 22A-C, marker lines 24A-C, marker pointers 25A-C, and total range of shield heights 41. In some cases stand 20 of FIGS. 2A-B may be or have the same components described for stand 20 of FIG. 1.

FIGS. 2A-B show shield 18 movably mounted between inner surfaces of rails 26, while FIG. 1 shows shield 18 movably mounted on a front surfaces of rails 26. According to embodiments, the shield may be movably mounted either way, such as by being movably mounted either way in either figure. Shield 18 may be moved to any of heights 41 along vertical height direction SMOV, such a by moving on or between rails 26 between strap 31 and base 32. Shield 18 may be movably arranged along surfaces of rails 26 over heights 41 to be positioned at height 40 selected based on a height of anatomy of the patient that is desired to be imaged, the position/area of the desired images, and the number of images, so that the markers provide software recognizable marks in images including the image areas for connecting the images. The markers may provide the marks, such as by marking or identifying vertical borders of image areas; and/or allowing the user to image enough overlap of a border in two adjacent images for computer software to automatically recognize the markers and/or overlap to accurately combine the images to form a single image including the two areas.

In some embodiments, right and left outer shield support rails 26 are rigid metal tracks and part of the stand structure connected to the base of the stand. Patient shield is held within these outer side rails and travels up and down them, such as with a resistive friction for example that is based on felt type of material lined inside of rails to provide sufficient friction to hold the shield from slipping once a desired height is set. In some cases, shield 18 may be mounted or attached to rails 26 by movable mounts such as wheels, bearings, or flanges that extend into and move along recesses in the inner or front surface of the rails. These mounts may roll or slide within or along the rails while they maintain mounting of the shield on the rails. In some cases, the mounts may form a shape around sides of the rails, such as a "C" shape that maintains mounting of the shield on the rails.

The vertical position or height 40 of the shield may be maintained on rails 26 such as by an anchor, pulley, or friction. For instance, a clamp or other mechanism may be manipulated by the user to lock the shield at height 40. In some cases, a pulley may counter the weight of the shield so that it does not move once stopped at position 40 by the user. In some cases, an amount of friction between the mount on the shield and the rails will maintain the position of the shield once it is stopped at a position by the user. Maintaining the position of the shield may include maintaining it with enough force to support the patient as described herein.

Shield 18 may support the patient, and optionally cooperate with handles or armrests 37 for supporting arms of the patient. Armrests 37 are shown coupled to rails 26, and may be foldable handles for resting the patient's arm on, such as know in the art. The armrests may be height adjustable, slidingly mounted on the rails similar to how the shield is mounted. In some cases, the armrests may be attached to shield 28 and move with the shield. In other cases, the armrests may move independently of the shield, in directions SMOV to be just below the height of shoulders or elbows of the patient to support the patient's arms or forearms.

Shield 18 may include fixed or typically preferred stick on or moveable markers 22 such as special shapes of marker material to identify (e.g., provide, demarcate, or mark) borders within overlap area of or between vertically adjacent radiographic image areas. Markers 22 may be arranged at horizontally wide enough (e.g., spread out) positions with respect to the patient's width so that the markers do not overlap with the image of the patient (e.g., anatomy) taken by the detector and/or so that they are not cut out of the imagable field when x-ray source field is collimated close to outer edges of desired region of interest patient anatomy. Markers 22, may have a cross shape, or any specific recognizable shape preferred by image processing software, such as those known in the art. For some embodiments, an "X" or "+" plus sign marker may be positioned on the right and left side of the outer edge of the area of the shield (e.g., at a horizontal outer border of the shield) where the multiple images will be captured at an overlap to each other. Each marker 22 may have a size determined by software preferred tolerances for example of at least 10 mm or larger or similar. The markers may be described as "stitching markers" to align or stitch together the adjacent multiple images, image borders, image edges, or image boundaries, as known in the art.

Shield 8 may also include marker lines 24 such as lines of radiation transparent material (low attenuation coefficient, not visible in the resulting image) to be used as Detector Alignment Markers, such as by identifying borders of radiographic image areas (e.g., in addition or independently of markers 22). Shield 18 may also include marker pointers 25 outside or within of the field of detectable view. If within field of view, such as shapes of radiation transparent material (low attenuation coefficient, not visible in the resulting image) These markings to be used as Side of Stand Alignment Markers, such as by being at the same height as markers 22, but on side or back surfaces of shield 18 to identify borders of radiographic image areas (e.g., in addition to and corresponding with the height of markers 22). The marker pointers may be attached to the front surface, side or back of the shield; or disposed through the shield to be visible to the user from the side and back of shield. In some cases, the pointers may be shaped like a nail, arrow, or pointer protruding the stand pointing backwards towards the detector. Pointers 25 may allow the user to more easily identify the height of the markers (and marker lines) from a position beside or behind the shield. This allows the user to more conveniently and efficiently move and locate detector 16 for the image areas. In some case, pointers 25 may be markers or markings that extend to or include markers on the back of the shield to assist user in locating the detector to the correct height position based on shield markings 22, such as by having pointers 25 at the same height as shield markers 22 on the front of the shield. Markers 25 may have a shape and size similar to that described for markers 22.

Stitching Markers 22 (A, B, C) typically are formed of (Pb) lead (which has large x-ray attenuation coefficient) so that they are recognizable in the image by the software which utilizes them to align the images and stitch or seam the adjoining images together. Markers 22 may be or include other substance with a large radiation attenuation coefficient. Being recognizable by the software be included in or a result of the markers identifying a border of an image area. Detector Alignment Markers or marker lines, 24 (A, B, C) are formed with x-ray transparent material (low x-ray attenuation coefficient, not visible in the resulting image) such as simple screen printed lines on the shield. Side of Stand Alignment Markers, or marker pointers 25 (A, B, C) may include a metal or plastic or similar material and act as visual mechanical guides (e.g., for the user) near or touching the shield alignment to the detector, to additionally simplify aligning the detector to the shield, (these are not in the image area and do not require any special material).

Markers 22 are shown in FIG. 2A as markers 22A identifying a border between image areas 42A and 42B; and markers 22B identifying a border between image areas 42B and 42C. In some cases, these borders may be used to mark images so that adjacent images can be combined (e.g., automatically or manually, using software) and/or to allow the user to position the detector to ensure enough image area exists over a border so that adjacent images can be combined (e.g., automatically or manually, using software). Marker lines 24 (e.g., Detector Alignment Markers) are shown in FIG. 2A as marker line 24A identifying a border between image areas 42A and 42B; and marker line 24B identifying a border between image areas 42B and 42C. In some cases, these borders may be used to position the detector to correct image areas (e.g., as noted above for markers 22A-B) so that adjacent images can be combined. Marker pointers 25 (Side of Stand Alignment Markers) are shown in FIG. 2B as marker pointer 25A identifying a border between image areas 42A and 42B; and marker pointer 25B identifying a border between image areas 42B and 42C. In some cases, these borders may be used to position the detector to correct image areas (e.g., as noted above for markers 22A-B) so that adjacent images can be combined. In some cases, the width between markers of markers 22A and B is selected based on the width of patient M and or the width of a desired total image area.

Although positions 38A-C and areas 42A-C are shown as three corresponding positions/areas, they may represent two or more corresponding adjacent positions/areas. In some cases they may represent only two corresponding adjacent positions/areas, such as 38A/B and 42A/B. In some cases, markers 22 may optionally include markers at the top border of area 42A and/or at the bottom border of area 42C (e.g., such as shown in FIG. 1). As shown in FIGS. 2A-B, some embodiments include markers 22C, marker lines 24C and marker pointers 25C, such as for identifying a border between area 42A and an area above area 42A. In some cases, markers 22C, lines 24C and/or pointers 25C may define a border between image area 42A and a similarly sized additional image area above area 42A. This additional image area may be used to image more height of a tall person or from floor to waist such as in long leg exams, or the typical image is for scoliosis exams covering the neck and spine. In these cases, the height of the patient's long leg exam area, or the height of the neck and spine for typical images for scoliosis may be considered the height of anatomy desired to be imaged. In some embodiments, markers 22 may be positioned on shield 18 as known in the art.

In some cases, descriptions herein of the use of "markers" or "markers 22" include the use of markers 22 and pointers 25. In some cases, descriptions herein of the use of "markers" or "markers 22" include the use of markers 22, lines 23, and pointers 25. In some cases, descriptions herein of "markers 22" include alignment lines at the same vertical height described for markers 22. In some cases, descriptions herein of "markers 22" include mid-level markers between adjacent vertically positioned markers 22 and at the left edge and right edge of shield 18 (e.g., not shown). The mid-level markers may be used to identify a vertical height for alignment of the x-ray tube to the center of each image area, such as by aligning the vertical center of the tube's output radiation and/or by using it's laser centering line (if it includes one) with the mid-level marker for an image area. These mid level markers may include marker pointers that function similar to pointers 25, and help with detector and/or source vertical alignment. Other appropriate positions of markers are also considered.

According to embodiments, based on the relative locations of markers 22 on the shield, the height range of anatomy of a patient that is desired to be imaged and desired area 44, the shield 18 can be moved to height 40 so that the marker positions in images of image areas 42A-C can be used for combining the images (e.g., areas 42A-C) of total image field 44 of patient M by overlapping the vertical location of a pair of markers 22A, B, or C as shown in adjacent figures. Moving to height 40 may also be based on ensuring that there is enough overlap of images of image areas of field 44 for connecting the images. The markers may be located with respect to each other on the shield so that the markers divide the total shield height into multiple vertical image areas, such as by demarcating, marking, or define a border of or between two image areas. Each image area may be described as an image "capture", "field", "view", or "frame". In some cases, the markers are easily located by the user or a computer in each of the images of an image area.

Control unit 23 or movement switches may be used to align multiple images or image areas of a total image or total image area, such as described herein. In some cases, control unit 23 may be connected to a digital x-ray workstation that features the ability to display, reprocess and send images to diagnostic workstations. In some embodiments, the alignment between vertically adjacent images (e.g., of image areas 42A-C) is recognized by software of digital x-ray workstation, by utilization of the special shapes of makers 22 or without markers identifying a specified typical overlap area and or recognition of anatomic structure. Once the separate images are captured, the software looks for the markers and lines them up with the sequential images captured, to accurately reproduce the overlap and align them together. In some cases, a different workstation or computer may be used to aligning the multiple images.

In some cases the imager may be a typical size such as 14 inch tall by 17 inch wide or square such as 17×17" flat panel detector. In typical uses the detector may be oriented for 14 inch wide by 17 in tall images. In some embodiments, the stand may be designed with its lines configured for 14×17 or 17×14 detector use. Height and width of stand and/or shield are not dependent on detector size. Height can be based on typical patient height ranges needed. Width can be based on typical widths of chest buckys and/or detectors common which currently utilize larger size detectors for these types of exams (DR, CR or film screen) such as 17×17 or 14×17 or similar. Detector stands that feature removable detector, typically will hold any size detector. As an example a 14×17 or 17×17 embodiment may feature a stand 78 inches high, and 29 inches wide; the shield may be 48 or 51 inches high and 14, 17 or 26 inches wide; the image areas defined by the markers may be 17 inches high with the center of marker overlap areas positioned at 15.5 inches and the adjustable width between markers may be 12 inches typical more or less based on patient width. In some cases, the space above markers 22C to the top of the shield may be 1 or more or less inches or even flush with the line; and the space from a marker to an image centerline marker may be center of a 14 or 17 inch depending on orientation. Some embodiments of stand 20 may apply to a 17 inch tall by 17 inch wide flat panel detector to provide wider anatomy coverage. In some embodiments the stand may fit either 14×17 portrait orientation or 17×17 without changes to the markings or stand dimensions. Stands may be designed for any size detector.

Figure 3A:
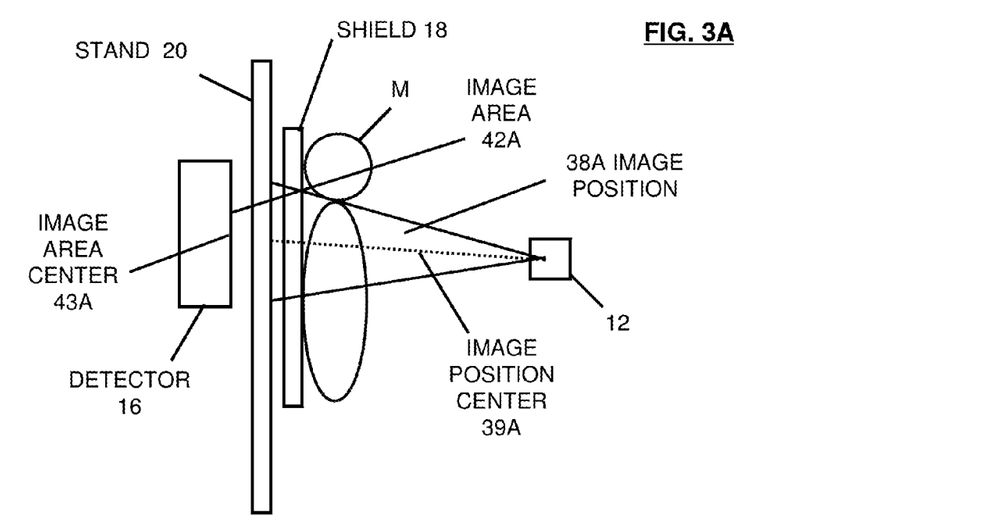
FIGS. 3A-B are side views illustrating example embodiments of a system for taking a long length of image of a spine using a patient positioning system for multiple image areas of a total radiographic image area or field.
Figure 3B:
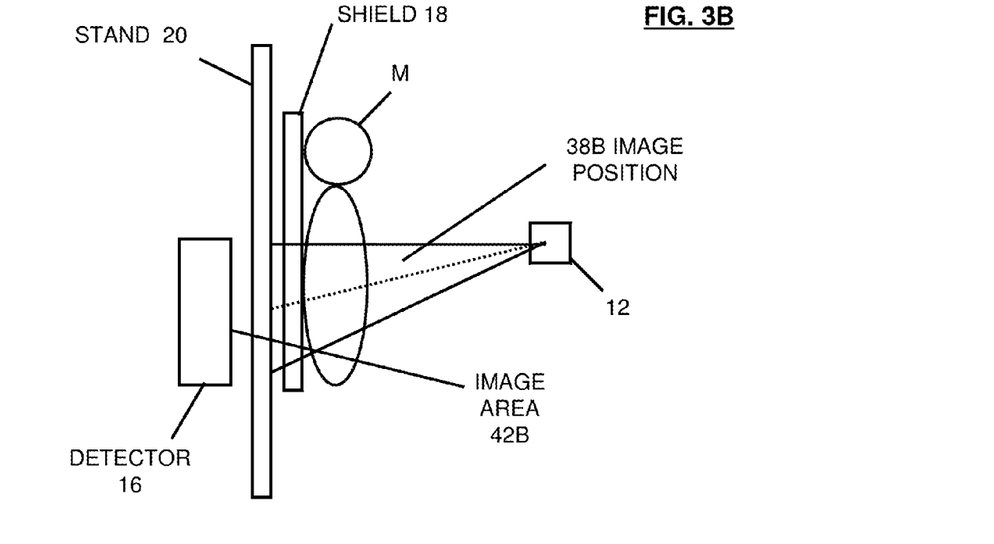
Figure 4:
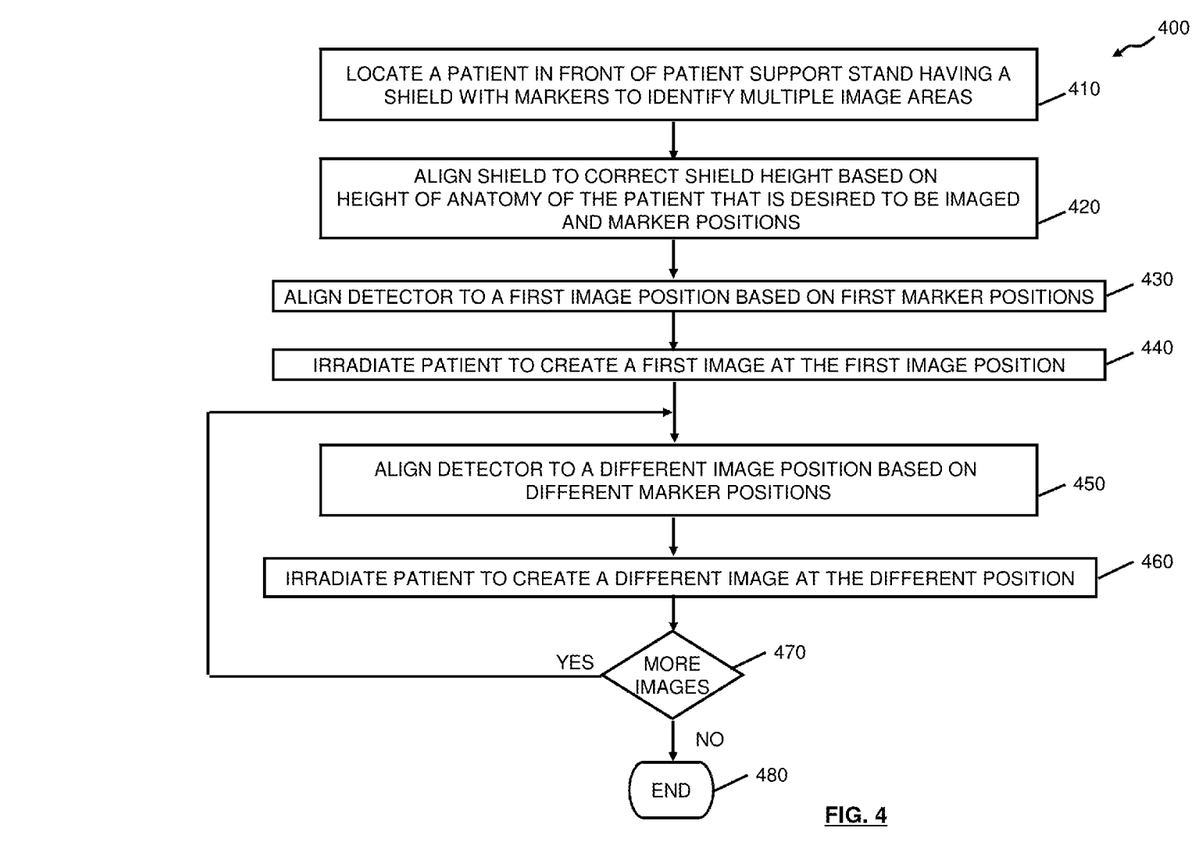
FIG. 4 shows example embodiments of a process for taking a long length of image of a spine using a patient positioning system for multiple image areas of a total radiographic image area or field.

FIGS. 3A-B are side views illustrating example embodiments of a system for taking a long length of image of a spine using a patient positioning system for multiple image areas of a total radiographic image area or field. In some cases the process of FIGS. 3A-B may include using system 10 as shown in FIGS. 1-2. FIG. 4 shows example embodiments of a process 400 for taking a long length of image of a spine using a patient positioning system for multiple image areas of a total radiographic image area or field. In some cases the process of FIG. 4 may include using the system as shown in of FIGS. 3A-B.

At block 410 a patient is located in front of patient support stand having a shield with markers to identify multiple image areas. Block 410 may include locating or positioning patient M at standing location 14 as described herein. In some cases, block 410 includes, as illustrated in FIG. 3A, positioning the patient M to stand with his/her back against (e.g., touching and possibly supported by) the shield 18 (and optionally armrests 37).

In some cases, block 410 includes properly locating stand 20 between source 12 and detector 16 (e.g., detector stand 34), such as by horizontally alignment, as noted herein. This may occur before locating the patient. In some cases, the patent may be located on a stand or block place on the floor between arms of the base of device, in order to image lower parts of the patient, such as the patient's foot image.

Then (e.g., next in time during process 400), at block 420 the shield is vertically aligned (e.g. manually moved or positioned) to a correct height based on the height range of anatomy of a patient that is desired to be imaged and marker 22 vertical height positions. In some cases, block 420 may include manually vertically locating the shield to a desired height based on the desired total image area, and/or a desired height range of anatomy of a patient that is desired to be imaged (e.g., imaged within the total image area). This may include selecting height 40 so that anatomy of a patient desired to be imaged is vertically located within the vertical range of two or more image areas (e.g., within areas 42A-B, or 42A-C if 3 areas are needed). Block 420 may include manually vertically locating the shield at height 40 (possibly using handle 28) as described herein. In some cases, block 420 includes, as illustrated in FIG. 3A, manually moving the shield to a desired shield height to arrange markers 22 at borders of desired image areas of a total image area, based on a height range of anatomy of a patient that is desired to be imaged and a determined total image area 44. In some cases, Block 420 may include positioning or moving removable markers on shield 18 as described below.

Then, in some embodiments, source 12 may be moved up and/or down along a vertical axis (e.g., using motors and control unit 23) to locate the desired source height so that it is vertically at the same height as the center of total image area 44. For example, the shield may have been set in a height position, by the user (not illustrated) to enable detection of an X-ray at area 42A that has passed through the chest of the subject M. Here, the patient's chest may be in (e.g., define or describe) a height range of anatomy of a patient that is desired to be imaged. This process may be part of block 420.

Then, at block 430 the detector is vertically aligned (e.g., manually moved or positioned) to a first image position or area based on first marker positions. Block 430 may include manually vertically aligned the detector to an image position or area (e.g., area 42A) as described herein. In some cases, at block 430, detector 16 is manually vertically aligned or moved to a correct detector height to capture an image of a first image area (e.g., area 42A) based on marker positions 22. Block 430 may include aligning the detector to an image position (e.g., position 38A) so that the detector images an area including at least the first image area (e.g., area 42A). It may also include aligning the detector based on the vertical location of markers, lines, or pointers so that the detector images an area including at least the first image area (e.g., area 42A). In certain cases, block 430 may include aligning detector 16 based only on markers 22A, lines 24A, or pointers 25A. In some cases, detector 16 may be aligned based only on the position of marker pointers 25. FIG. 3A, illustrates and example where detector 16 may be manually set in a position by the user, enabling detection of an X-ray that has passed through the chest of the subject M, based on markers 24A and/or 25A. Aligning to the first position may include alignment of detector to 22C or 24A as a top of the image field reference, or aligning from the bottom up aligning the bottom of image area with the as a bottom of image area 42C or to marking 24B as the starting reference.

Then, at block 440 the patient is irradiated to create a first image at the first image position or area Block 440 may include aligning the radiation output beam of source 12 to an image position (e.g., position 38A) so that the beam radiates an area including at least the first image area (e.g., area 42A). It may also include aligning the source based on the vertical location of markers (e.g., markers 22A) and/or the height of the detector so that the detector images an area including at least the first image area (e.g., area 42A). Block 440 may include generating or creating an image of an image area (e.g., area 42A) as described herein. In some cases, at block 440, source 12 irradiates the patient and detector 16; and the detector captures an image of a first image area (e.g., area 42A) including marker positions 22. This image may include markers 22A; or 22A with markers 22B; or markers 22B.

For some cases of block 440, as illustrated in FIG. 3A, an X-ray is applied toward the chest of the subject M from the X-ray source 12 to take an image of the upper half of the spine. In this case the upper half of the spine may be in a height range of anatomy of a patient that is desired to be imaged. For example, source 12 may be aligned to provide image position 38A, such as by vertically aligning height of image position center 39A with that of image center 43A of area 42A.

Block 440 may also include cases where detection signals that have entered detector 16 and are detected by the detector are sent to the detector workstation or detector control unit (not shown). The detector workstation or detector control unit converts the received detection signals to digital signals to generate image data and temporarily stores it in memory (not illustrated). Each of these radiographic images may include images of the markers at its part overlapping the other radiographic image, together with an image of the subject M.

Then, at block 450 the detector is vertically aligned (e.g., manually) or moved to a different (e.g., different than the first) image position or area based on different marker positions. Block 450 may include manually vertically aligned the detector to an image position or area (e.g., area 42B) as described herein. Block 450 may include generating or creating an image of an image area (e.g., area 42B) as described herein. The different image area may be an image area adjacent to the first area, and that shares a common or same set of markers 22 on shield 18 (e.g., markers 22A). In this case, the detector is manually vertically aligned or moved to a different (e.g., different than the first) image position or area based on the same marker positions. In some cases, at block 450, detector 16 is vertically aligned or moved to a correct detector height to capture an image of a second image area (e.g., area 42B) based on marker positions 22. In certain cases, block 450 may include aligning detector 16 based only on lines 24B, or pointers 25B. Appropriate other descriptions above for block 430 may apply to block 450.

For some cases of block 450, as illustrated in FIG. 3B, the shield and source are not moved vertically (e.g., along a vertical axis) since they are already at a desired shield height, such as noted for FIG. 3A. This may save time during the process. In some cases, the patient is not re-located. Thus, if the patient does not move by error (during the shortened process), the markers and patent anatomy (e.g., of the desired total image area) should remain the same. This allows the images of the different image areas to be more accurate compared to each other and to be more accurately stitched together. For example, the shield may have been set in FIG. 3A to a height position, by the user to also enable detection of an X-ray at area 42B that has passed through the abdomen of the subject M.

For some cases of block 450, as illustrated in FIG. 3B, detector 16 is set in a position by the user, enabling detection of an X-ray that has passed through the abdomen of the subject M, based on markers 22A and/or 22B. In this case for example the abdomen may be in a height range of anatomy of a patient that is desired to be imaged.

Then, at block 460 the patient is irradiated to create a different image at the different image position or area. Block 460 may include generating or creating an image of an image area (e.g., area 42B) as described herein. In some cases, at block 460, source 12 irradiates the patient and detector 16; and the detector captures an image of a different image area (e.g., area 42B) including marker positions 22. This image may include different markers 22B. Appropriate other descriptions above for block 440 may apply to block 460.

For some cases of block 460, as illustrated in FIG. 3B, the direction of the X-ray applied from the X-ray source 12 is changed (e.g., rotated in direction ROT) with the positions of the markers (e.g., markers 22B) to apply the X-ray toward the abdomen of the subject M, thereby taking an image of the lower half of the spine. For example, source 12 may be aligned to provide image position 38B, such as by vertically aligning height of image position center with that of image center 43 of area 42B.

Block 460 may also include cases where detection signals that have entered detector 16 and are detected by the detector are sent to the control unit 23. The detector workstation or detector control unit converts the received detection signals to digital signals to generate image data and temporarily stores it in memory (not illustrated). Each of these radiographic images may include images of the markers 22B at its part overlapping the other radiographic image, together with an image of the subject M.

At decision block 470 it is determined whether more images are desired. Block 47 may include determining base on a desired total image area or a planned image area as described herein. In some cases, one or more additional images are desired, such as where the first and additional images of blocks 440 and 460 do not provide image areas of a sufficient or desired total image area. Block 470 may include the user making the determination that more images are or are not desired based on the desired total image area.

If more images are desired, process 400 returns to block 450. In this case, process 400 may continue for another set of different image positions. This other set of different images may include or be to create an image of image area 42C. This continuation may include process describe above for blocks 450-460, but apply to area 42C and markers 22B. It is considered that in some case, a fourth image may be desired to form the desired total image area. Thus, in some cases, the imaging process can be repeated for the number of images required to capture the desired full length of region of interest. Some typical exams may be accommodated with 1 to 3 images. In some embodiments, additional length may be accomplished with a taller stand design with additional detector lengths based on the overall length of the stand.

If more images are not desired, process 400 continues to block 480 and the process ends. Block 480 may include connecting the image areas into a total image area, such as using detector workstation. For example, one or more image areas may be connected or "stitched" together by vertically aligning markers 22 located on shield 18 between adjacent image areas.

The images may be connected by connecting the image vertical borders, such as by overlaying vertical borders of two adjacent images (e.g., automatically in a computer, or manually by aligning the borders on a display, such as using a computer input or mouse) so that the markers shared by borders (e.g., markers 22A or 22B) of adjacent images of adjacent image areas are overlayed in the images. Such overlaying may include aligning the markers in one image to be displayed over the same markers displayed in the adjacent image, such as is know in the art.

In some cases of block 480 (e.g., in the detector workstation) the image of area 42A (e.g., the upper half of the spine that has been taken first) and the image of area 42B (e.g., the lower half of the spine that has been taken later) are read from the memory, and aligned based on the markers 22A shown within the overlapping parts of the images to connect the two images (e.g., thereby providing one long-length image showing the entire spine). Here the entire spine may define the height range of anatomy of a patient that is desired to be imaged. For cases where image area 42C is also to be connect (e.g., in the detector workstation) the image of image area 42C is read from the memory, and aligned based on the markers 22B shown within the overlapping parts of the images to connect the third image to the other two images. Thus, at block 480, images of image areas 42A and 42B (and optionally 42C) may all be connected (e.g., combined or stitched together) to form an image of total image area 44, such as a desired long length image of a desired total image area.

According to embodiments, x-ray imagable markers 22 may be removable markers that are removably and reusably adhered to shield 18, such as markers having an adhesive backing, adhesive strip, stick adhesive, sticky substance or other structure for temporarily adhering the markers to the surface of shield 18, so that the maker can be easily removed and repositioned on the shield, without inadvertently being knocked or bumped off by the patient or falling due to gravity during an imaging procedure to obtain total image area 44. Removable markers may be manually moveable or positioned so that the markers can be laterally/horizontally moved for different width anatomy or patients.

In some cases, the removable markers may be positioned at the same vertical position shown in FIGS. 1-3, but are adhered by the user based on a width of the patient, and placement along the outer area of the image and within the area of adjoining image to image overlap, or the combination thereof.

In some cases, the removable markers may be positioned at the different vertical position that those shown in FIGS. 1-3, but are adhered by the user based on a height range of the size of the detector or its height orientation, or the combination thereof. This case may apply where the height range of anatomy of a patient that is desired to be imaged is greater or less than areas 42A-C covered by existing heights of markers 22 for a desired total image area.

By being able to manually move or positioning stand 20, shield height 40, and/or height of detector 16, embodiments described herein may provide benefits of reduced complication, improved speed of transition from one image location to the next, reduced patient movement, improved accuracy of detector positioning and stitching process, reduced costs and time during procedures. They may also lower cost and complexity of system 20. In addition, they may result in fewer inaccuracies in the images and total image area; and more efficient use of the system. They may also provide a more intuitive, efficient and hands on feel and use of the system by the user. They may result in a system that is more versatile, costs less, has fewer components, has less software, has less stitching mistakes and/or better image quality, provides more accurate images, operates more quickly and is easier for the user to use. These benefits are as compared to systems that do not manually move or locate stand 20, shield height 40, and/or height of detector 16; such as systems that automatically (e.g., by computer or controller) move the stand, shield, and/or detector.

Instead, according to embodiments, the height of the shield and detector can be manually aligned instead of being computer controlled. For example, in some cases, (1) the height of the shield can be independently adjusted (e.g., with respect to the detector) for the patient height, (2) while maintaining marker positions (or using moveable marker positions) on a movable shield that are disposed at fixed height positions with respect to each other, to demarcate or identify a plurality image areas; (3) of different imaging positions for the detector, that are selected/planned to be imaged by the user.

In some cases these benefits may be realized by a system where only shield 18 is manually moved or positioned (e.g., based on height range of anatomy of a patient that is desired to be imaged, and the other components are automatically positioned). In some cases these benefits my result be realized by a system where only shield 18 and detector 16 are manually moved or positioned (e.g., based on height range of anatomy of a patient that is desired to be imaged, and the other components are automatically positioned).

The foregoing description of embodiments of the invention has been presented to illustrate the principles of the invention and not to limit the invention to the particular embodiment illustrated. It will, however, be evident that various modifications and changes may be made thereto without departing from the broader spirit and scope of embodiments of the present invention. For instance, portable stand devices, systems, methods of use, and means for performing stand functions and other uses of the stand technologies described herein are considered as possible embodiments of the invention. Moreover, the foregoing stand structures are provided by way of example as they structures used for such a portable stand with an adjustable height shield on rails. It will be appreciated that other structures may be used for the stand, such as where only one rail is used instead of two. It may also be appreciated that long length imaging can be used for other than human imaging. The present specification and figures are accordingly to be regarded as illustrative rather than restrictive. It is intended that the scope of the invention be defined by all of the embodiments encompassed within the following claims and their equivalents.

The invention claimed is:

1. A mobile positioning stand for positioning a patient to image a total radiographic image area of the patient, the stand providing multiple radiographic image areas of the total radiographic image area, the total radiographic image area being longer than a length of each image area, the stand comprising:
   a frame having two parallel vertical rails; and
   a shield movably coupled to the rails to be motorized or manually moved along a vertical path, the shield having a radio transparent material, the shield having markers, the shield being movably coupled to the rails to be manually moved to a shield height position, based on a height of anatomy of the patient desired to be imaged, the shield height position selected so that the markers provide marks for aligning an image detector to correct positions for imaging vertically adjacent and partially overlapping images of vertically adjacent image areas of a desired total image area of the patient.

2. The mobile positioning stand of claim 1, wherein the markers identify the multiple radiographic image areas of the total radiographic image area, the total radiographic image area being longer than a length of each image area, the desired total image area formed by connecting a plurality of images of the multiple image areas.

3. The mobile positioning stand of claim 1, wherein the shield includes an ability to be manually gripped by a user to vertically move the shield along the rails to locate the shield at a desired shield height that positions the markers at vertical borders of the multiple image areas.

4. The mobile positioning stand of claim 1, further comprising:
   a patient standing location in front of the shield for positioning a patient to image the desired total image area of the patient using the stand,
   wherein the shield is positioned one of (i) between the patient and the rails, or (ii) behind the patient and between the rails.

5. The mobile positioning stand of claim 4, wherein the stand includes:
   a base below and attached to the rails, the base having arms with wheels for rolling on a floor; and
   a top strap above and attached to the rails to support the shield and movements of the shield,
   wherein the base and top strap extend between the rails, and wherein the patient standing location is between the arms of the base.

6. The mobile positioning stand of claim 1, wherein the shield further comprises stitching markers including a substance with a large radiation attenuation coefficient, the stitching markers at locations used for connecting vertically adjacent images of the vertically adjacent image areas of the desired total image area of the patient.

7. The mobile positioning stand of claim 1, wherein the shield is slidingly mounted on the rails to allow the shield to move to a position, based on the height of the anatomy the patient desired to be imagined, the positions and areas of desired images, and a number of desired images.

8. The mobile positioning stand of claim 1, wherein the markers are located at boundaries of the vertically adjacent image areas of the desired total image area of the patient.

9. The mobile positioning stand of claim 1, wherein the markers are arranged at vertical levels, at borders between the vertically adjacent image areas, each vertically adjacent image area comprising a maximum imagable area of the imager, and further including pointer markers at a same height as the markers, the pointer markers disposed on the shield or outer side edges of the shield to assist a user in vertically locating the detector to a correct vertical position based on the pointer markers, for aligning the detector to correct positions for each vertically adjacent image area.

10. The mobile positioning stand of claim 1, wherein the shield is slidingly mounted on the rails to allow a height of the shield to be independently adjusted for the height of the anatomy of the patient, with respect to the detector; and wherein the makers are positioned on the shield at fixed height positions with respect to each other to demarcate a plurality of different imaging positions of the detector, that are desired to be imaged by a user.

11. A system for positioning a patient to image a total radiographic image area of the patient, the system providing multiple radiographic images of multiple image areas of the total radiographic image area, the total radiographic image area being longer than a length of each image area, the total radiographic image area formed by connecting a plurality of images of a plurality of image areas, the system comprising:
   a movable positioning stand comprising:
      a frame having at least one vertical rail;
      a shield movably coupled to the stand to be manually moved along a vertical path, the shield having a radio transparent material, the shield having markers including a substance with a low radiation attenuation coefficient, the shield being movably coupled to the stand to be manually moved to a shield height position, based on a height of anatomy of the patient desired to be imaged, the shield height position selected so that the markers provide marks for aligning an image detector to correct positions for imaging vertically adjacent and partially overlapping images of vertically adjacent image areas of a desired total image area of the patient; and
      a base below and attached to the rail, the base having wheels for rolling on a floor to locate the stand between the patient and a flat panel image detector mounted on a detector stand behind the positioning stand, the detector movably coupled to the detector stand to be manually moved vertically along a vertical axis to be positioned at a vertical position based on a vertical position of the markers, the detector to receive radiation emitted by a radiation imaging source in front of the stand and patient.

12. The system of claim 11, wherein the shield further comprises:
   removable imagable markers manually located on the shield based on a patient width and planned image positions of the desired total image area, the removable markers to be detected by a control computer for generating images from data received from the detector, the computer for connecting vertically adjacent images of the vertically adjacent image areas based on the removable markers.

13. The system of claim 11, wherein the source of radiation is positioned at a vertical height that is a same height as a center height of the total radiographic image area.

14. The system of claim 11, wherein the markers are at vertical borders of multiple radiographic image areas of the total desired image area, the desired total image area being longer than a length of each of the plurality of image areas, the total image area formed by connecting a plurality of images of the plurality of image areas.

15. A method of using a positioning stand to position a patient and to locate a radiographic detector at multiple positions to create multiple images of multiple image areas identified by markers of a shield of the stand, the method comprising:

locating the patient in front of the stand;

manually vertically aligning the shield of the stand to a shield height based on a height of anatomy of a patient desired to be imaged for a desired total image area; and vertically aligning a detector height to a first detector height position based on first marker positions.

16. The method of claim 15, further comprising:

angling or vertically elevating a radiation source to the first detector height position;

irradiating the patient to create a first image at the first detector height position;

aligning the detector to the second detector height position based on the first marker positions;

angling or vertically elevating the radiation source to the second detector height position; and irradiating the patient to create a second image at the second detector height position.

17. The method of claim 16, further comprising vertically centering a height of the radiation source to a height of a vertical center of the shield or total image area.

18. The method of claim 16, wherein first markers at the first marker positions are imaged in the first and second images; and further comprising:

vertically aligning the first and second images to form a desired total image including the desired total image area.

19. The method of claim 18, further comprising:

aligning the detector to a third detector height position based on second marker positions;

angling or vertically elevating the radiation source to the third detector height position;

irradiating the patient to create a third image at third a detector height position, wherein second markers at the second marker positions are imaged in the second and third images; and vertically aligning the second and third images to form the desired total image including the desired total image area.

20. The method of claim 15, wherein vertically aligning the detector height comprises manually vertically aligning the detector height based on marker pointer positions that are visible from one of the front, side or back of the shield, to demarcate accurate alignment locations for the detector to each of the multiple image areas.

21. The method of claim 15, wherein manually vertically aligning the shield comprises:

manually vertically aligning the shield based on vertical positions of three sets of the markers on the shield, locating a range of height of the anatomy of the patient within a range of height of a desired number of image areas within the vertical positions of the three sets of markers, and manually vertically aligning the shield based on a desired number of image areas.

22. The method of claim 15, wherein manually vertically aligning the shield includes:

locating a range of height of the anatomy of the patient within a range of height of a desired number of image areas within the vertical positions of three sets of markers; and independently adjusting a height of the shield with respect to a height of the detector, wherein the makers are positioned on the shield at fixed height positions with respect to each other to demarcate a plurality of different imaging positions of the detector that are desired to be imaged by a user, and further comprising:

independently adjusting the height of the detector based on a height of the markers, after aligning the shield.

23. The method of claim 5, wherein manually vertically aligning the shield includes manually locating removable imagable markers onto the shield based on a patient width and planned image positions of the desired total image area.

* * * * *